US00PP10547P

United States Patent [19]

Bjorge et al.

[11] Patent Number: Plant 10,547

[45] Date of Patent: Aug. 11, 1998

[54] 'FA 59' PEACH TREE

[75] Inventors: Annette Bjorge; Randy Bjorge, both of Coloma, Mich.

[73] Assignee: International Plant Management, Lawrence, Mich.

[21] Appl. No.: 738,251

[22] Filed: Oct. 28, 1996

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new peach variety, *Prunus persica*, (hereinafter referred to as the 'FA 59' peach tree) which was developed by Annette and Randy Bjorge in a breeding program at Fruit Acres Farm in Coloma, Mich., having the following combination of unique and desirable features:

1. A very large, substantially round fruit with clear yellow flesh and very attractive orange-red stripe over a red blush covering 80% of the fruit at maturity.
2. A fruit maturing 20 days later that the 'Redhaven' peach.
3. A fruit with flesh that does not brown when cut.
4. A fruit with excellent shipping and storage qualities.
5. A fruit that ripens with multiple pickings and produces heavy tonnage per acre.

3 Drawing Sheets

ORIGIN OF THE VARIETY

The new variety of peach tree 'FA 59' was developed by Annette and Randy Bjorge in a peach breeding program at Fruit Acres Farms, 2559 Friday Road, Coloma Mich. 49038. The 'FA 59' peach tree was developed as a first generation cross between 'Fayette' and 'SH 426'. 'Fayette ' being an established, non-patented, commercial variety and 'SH 426' being a numbered test variety from the South Haven Research Station, South Haven Mich. This research facility is no longer in operation. The parent tree was grown and maintained in a peach tree breeding orchard on Fruit Acres Farms. This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of large, open, upright growth with medium density and is a regular and very productive bearer of peaches. The new variety produces very large fruits that ripen with multiple pickings and produce a high per acre tonnage. The fruit of the new variety is characterized by very large, round, freestone, substantially 80% orange-red fruits with a mottled striping pattern on the exposed parts of the fruit that bleed into a glowing red blush. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling. The tree and fruits of the new variety exhibit good resistance to Bacterial Spot and are very cold hardy. The fruit matures in the middle of the peach growing season in Southwestern Mich. It ripens 20 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Mich.

FIG. 1. illustrates specimens of the fully ripened fruit and foliage of the new variety.

FIG. 2. illustrates blooms of the new variety.

FIG. 3. Illustrates two specimens of the new variety. The lower specimen is bisected along the suture, the upper specimen is bisected as a ninety-degree angle to the plane of the suture. The color and forms of the flesh, pit and pit cavity are illustrated.

DETAILED DESCRIPTION OF THE VARIETY

Figure 1:
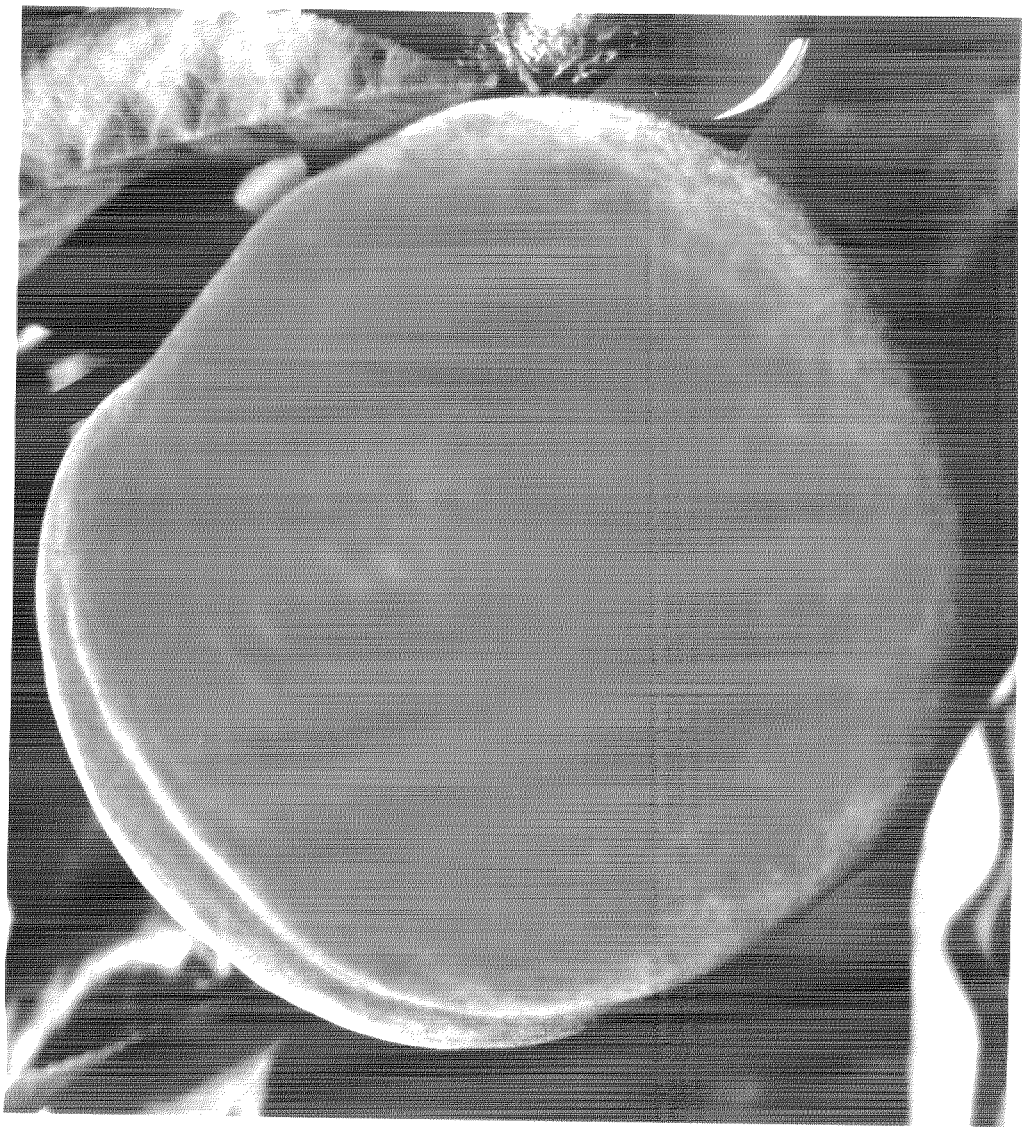
Figure 2:
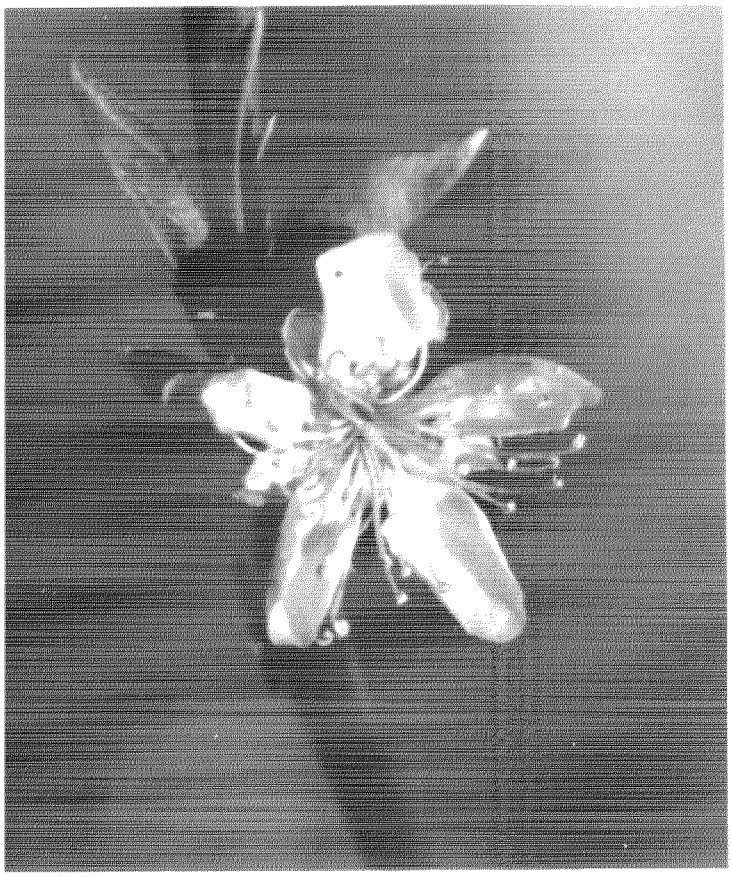
Figure 3:
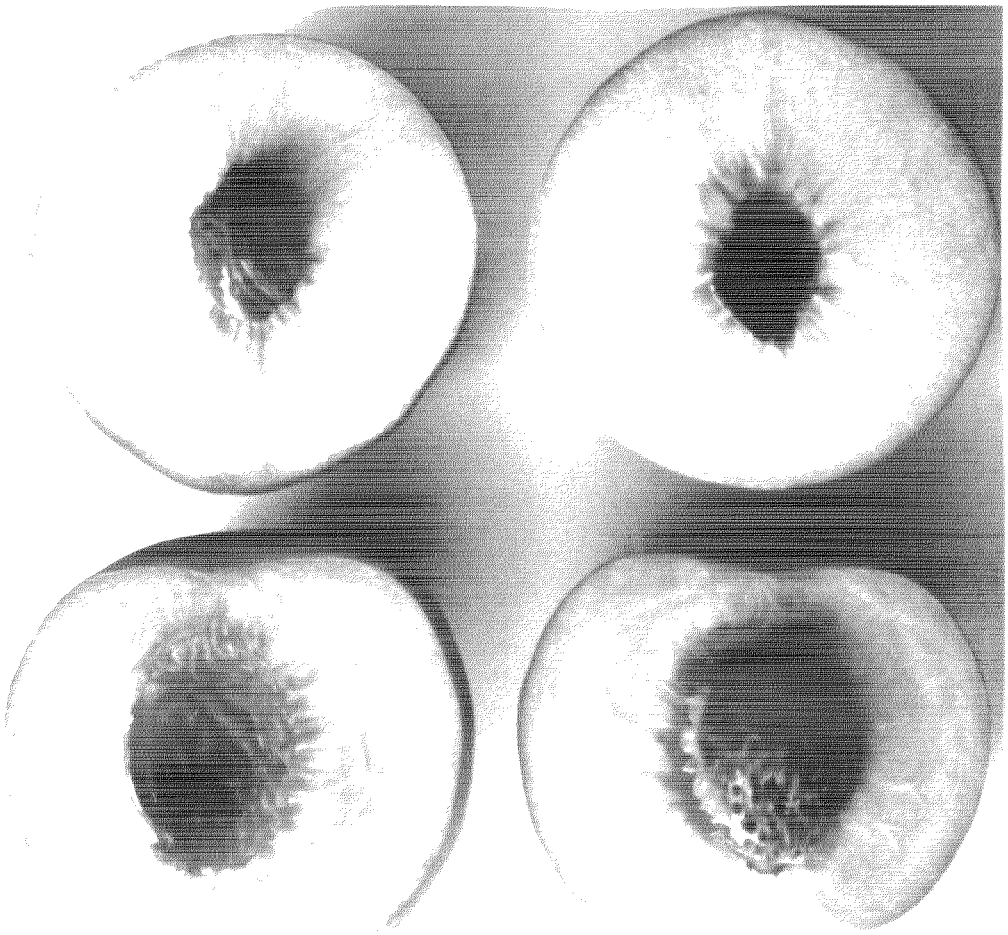

The following description of the fruit and foliage of the new variety is based on observations of specimens grown in Berrien and Van Buren County of southwestern Mich. The color terminology is in accordance with The Royal Horticultural Society Colour Chart, published by The Royal Horticultural Society of London, England.

Tree:

*Age of specimen*—15 years.
*Height*.—Unpruned 4.6M.
*Width*.—Unpruned 4.6M.
*Size*.—Large.
*Vigor*.—High, minimal thinning required. Fruits are naturally well spaced on the branches.
*Density*.—Open, internode length averages 1 to 1½ cm.
*Form*.—Upright, major scaffold branches form 35 to 45° angles to the trunk. Will form a central leader if left unpruned. Does not require supplemental support.
*Production*.—More productive than 'Newhaven', similar to 'Fayette', not as productive as 'Redhaven'.
*Bearing*.—Annual, ripens with two pickings with 70 % of the crop being mature for the first picking and 30% mature for the second picking. Mature fruits will hold on the tree for 10 days.
*Disease resistance*.—Resistant to bacterial spot.
*Cold hardiness*.—Very hardy.

Trunk:

*Size*.—Large.
*Surface*.—Smooth.
*Lenticils*.—Medium.

*Color.*—Gray 201 B.

Leaves:

*Size.*—Length 190mm, width 58mm.

*Form.*—Lanceolate, pointed.

*Thickness.*—Thick.

*Texture.*—Thick.

*Margin.*—Crenate.

*Petiole.*—Length 13mm, medium thickness.

*Glands.*—Reniform, 2 to 3 on upper petiole and lower leaf blade.

*Color.*—Upper surface Green 147 A, lower surface Green 147 B.

*Stipules.*—None.

Flower buds:

*Size.*—Medium.

*Length.*—Medium.

Flowers:

*Blooming period.*—April 8 to 15 in Coloma, Mich.

*Presentation.*—Medium showy.

*Pollen.*—Present, self fertilizing.

*Petals.*—5 in number, slightly cupped, 11mm long, 10mm wide, Purple-Red 73 A.

*Stamens.*—Slightly curved.

*Pistil.*—17mm, White 155 A.

Fruit:

*Maturity when described.*—Firm ripe.

*Date of first picking.*—August 17 in Coloma, Mich.

*Size.*—80 to 90mm.

*Form.*—Round.

*Suture.*—Inconspicuous.

*Pistil point.*—Inverted.

Skin:

*Thickness.*—Thin.

*Texture.*—Fine.

*Tendency to crack.*—None.

*Down.*—Moderate.

*Color.*—*Very attractive* 80% Red 47 A in a mottled striping pattern over virtually all of the exposed fruit bleeding into Orange 27 C.

Flesh:

*Texture.*—Fine.

*Aroma.*—very Aromatic.

*Fibres.*—Few, small, tender, not conspicuous or noticeable in eating.

*Color.*—Yellow orange 22 B., slight red around pit, Red 47 A.

*Coloration at the pit.*—Pinkish red bleeding into the flesh around 80 to 90% of the pit area.

*Eating quality.*—Best, very flavorful. Very sweet with medium acid.

Stone:

*Size.*—Length 32mm, width 25mm, thickness 18mm.

*Form.*—Ovate.

*Apex.*—Pointed.

*Sides.*—Nearly equal.

*Base.*—Slanted.

*Surface.*—Pitted to furrowed throughout.

*Color.*—Grayed-orange 175 A.

*Type.*—Freestone.

*Tendency to crack.*—*Some.*

Use: Desert, fresh and commercial market.

Shipping quality: Excellent.

Keeping quality: Excellent, will keep for 4 weeks in common cold storage.

Disease resistance: Good resistance to Bacterial Spot.

I claim:

1. A new and distinct variety of peach tree, *Prunus persica,* substantially as herein shown and described, characterized particularly as to novelty by the unique combination of a large size, very vigorous, upright, open, medium density, heavy bearing tree, with good resistance to bacterial spot, producing freestone fruits having clear yellow, nonbrowning flesh and substantially round, firm, very large, 80% mottled striped orange-red skin color at maturity which occurs 17 days after the maturity of 'Redhaven' peach.

* * * * *

FA 59